United States Patent [19]
Johnson

[11] Patent Number: 5,334,200
[45] Date of Patent: Aug. 2, 1994

[54] SUTURE KNOT MAKING DEVICE AND METHOD FOR USE

[75] Inventor: Lanny L. Johnson, 4528 Hagadorn, East Lansing, Mich. 48823

[73] Assignee: Lanny L. Johnson, Lansing, Mich.

[21] Appl. No.: 24,749

[22] Filed: Mar. 2, 1993

[51] Int. Cl.⁵ .............................................. A61B 17/00
[52] U.S. Cl. ..................................... 606/148; 606/139
[58] Field of Search ................... 606/1, 139, 144, 148

[56] References Cited

U.S. PATENT DOCUMENTS

| | | | |
|---|---|---|---|
| 5,041,129 | 8/1991 | Hayhurst et al. | |
| 5,084,058 | 1/1992 | Li. | |
| 5,087,263 | 2/1992 | Li. | |
| 5,133,723 | 7/1992 | Li et al. | |
| 5,163,946 | 11/1992 | Li. | |
| 5,176,691 | 1/1993 | Pierce | 606/148 |
| 5,217,470 | 6/1993 | Weston | 606/148 |
| 5,217,471 | 6/1993 | Burkhart | 606/139 |
| 5,234,444 | 8/1993 | Christoudias | 606/139 |
| 5,234,445 | 8/1993 | Walker et al. | 606/148 |

Primary Examiner—Stephen C. Pellegrino
Assistant Examiner—Jeffrey A. Schmidt
Attorney, Agent, or Firm—Cushman, Darby & Cushman

[57] ABSTRACT

A suture knot making device is provided including a cylindrical member having distal and proximal portions. The distal portion has a convexly curved end from which first and second bores are disposed through the cylindrical member. Each bore has a distal open end disposed substantially adjacent a transition area where the convexly curved end merges with the cylindrical surface of the device. The distal open ends are disposed approximately 180° apart. Each of the first and second bores extends at an acute angle relative to a longitudinal axis of the cylindrical member whereby the bore cross within the member without intersecting. When a suture is formed into a loop and at least one of its ends is passed through a bore from the distal end of the device and is held taut at the proximal end, the suture is tightly forced against the convexly curved end of the device to thereby permit a tight knot to be formed at the surgical site.

9 Claims, 3 Drawing Sheets

SUTURE KNOT MAKING DEVICE AND METHOD FOR USE

BACKGROUND OF THE INVENTION

1. Field of the Invention

The present invention relates to a surgical instrument for forming a suture knot in tissue at a surgical site remote from an opening leading to the site.

2. Description of Related Art

In both open and endoscopic surgery, it often is necessary to form a knot at a surgical site remote from an opening leading to the site. Tying an effective knot requires pulling the suture ends in a plane parallel to the surface of the tissue being brought together. The knot tying process requires a first loop to be self-retaining while subsequent loops are formed and moved to the desired knot location.

Securing the knot at the surgical site is dependent upon the nature of the suture material. Rough or compliant material is more likely to stay in place. Also critical in securing the knot is the knot tying technique. Pressure exerted on a single suture end during tying would produce an asymmetrical force tending to disrupt the surgical site. Thus, the optimum technique in forming a knot is to simultaneously pull in parallel both ends of the suture, thereby creating symmetrical pressure on the loop. However, in some types of surgical circumstances, and particularly when using a cannula as is customary in endoscopic surgery, it is not possible to manipulate suture ends in the plane of the tissue and pull them in a plane parallel to the tissue to be joined.

Known suture procedures for forming a knot at a remote surgical site typically involve forming a loop outside the opening to the site, moving the loop down the length of the passage to the site, forming a second loop in the suture outside the opening and moving that loop to the site so that it rests atop the first loop, and thereafter repeating the process, as required, so as to form the desired knot.

Attempts have been made to provide surgical instruments which aid in performing the foregoing procedure to approximate a parallel pull of suture ends in a plane parallel to the tissue to be joined. For example, U.S. Pat. No. 5,087,263 discloses a suture loop holder and run down system having a body with distal and proximal ends. The distal end has a concave shape for receiving loops of suture. However, the loops may loosen as they are delivered to the surgical site, because adequate pressure cannot be exerted on the loops due to the concave shape of the distal end of the holder. Thus, a tight knot may not be formed at the surgical site.

SUMMARY OF THE INVENTION

An object of the present invention is to provide a suture knot making device which permits suture loops to be formed at a location remote from a surgical site and then moved to the site, while remaining taut, to form an acceptable knot at the site.

A further object of the invention is to provide a suture knot making device which permits the suture to spread in the plane of the tissue to be joined whereby both ends of the suture can be pulled, as in normal tying.

In accordance with the principles of the present invention the foregoing objects are achieved by providing a suture knot making device comprising a cylindrical member having distal and proximal portions. The distal portion has a convexly curved end from which first and second bores are disposed through the cylindrical member. Each bore has a distal open end disposed substantially adjacent a transition area where the convexly curved end merges with the cylindrical surface of the device. The distal open ends are disposed approximately 180° apart. Each of the first and second bores extends at an acute angle relative to a longitudinal axis of the cylindrical member whereby the bores cross within the member without intersecting. When a suture is formed into a loop and its opposite ends are passed through the respective bores from the distal end of the device and are held taut at the proximal end, the loop is snugly held against the convexly curved end of the device to thereby permit a tight knot to be formed when the loop is positioned at the surgical site.

In accordance with a further aspect of the invention, an improved method is provided for forming a knot at a remote surgical site. A suture is passed through, around or into tissue to be joined, and the ends of the suture are delivered through an opening to the remote surgical site. Next, a loop is formed in the suture. One end of the suture is threaded through the first bore in the knot making device previously described, and the other end of the suture is threaded through the second bore in the device. The proximal portion of the device then is grasped, and the suture ends are drawn taut so that the loop is moved against the convexly curved distal end of the device. The device next is inserted into the opening to the surgical site to deliver the loop to the site, where increased pressure on the suture ends causes the knot to tighten. Finally, the suture ends are released, and the device is retracted from the opening. The process may be repeated, as required, to form multiple knots at the surgical site.

Other objects, features and characteristics of the present invention, as well as the function of the related elements of the structure, and economies of manufacture, will become more apparent upon consideration of the following detailed description and appended claims with reference to the accompanying drawings, all of which form a part of the specification.

DETAILED DESCRIPTION OF THE INVENTION

Figure 2:
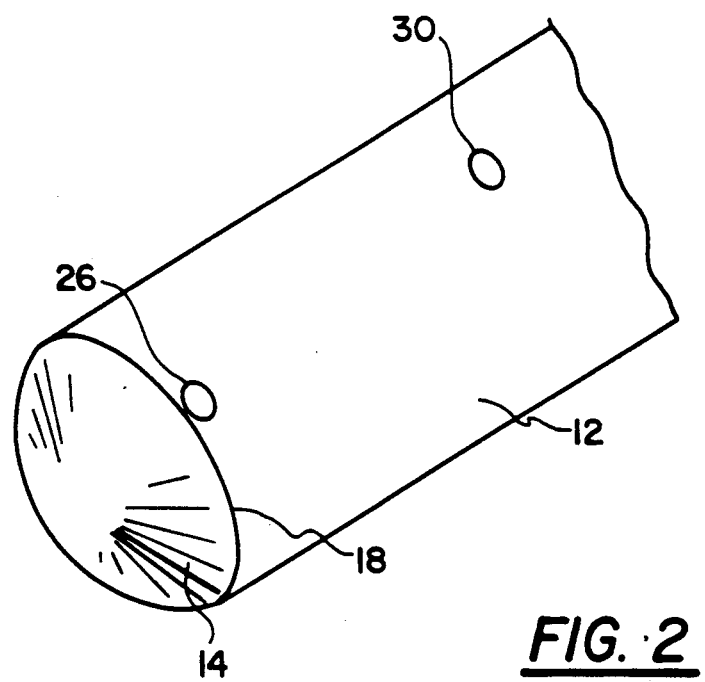
FIG. 2 is an enlarged perspective view of the convex distal end portion of the suture knot making device shown in FIG. 1.
Figure 3:
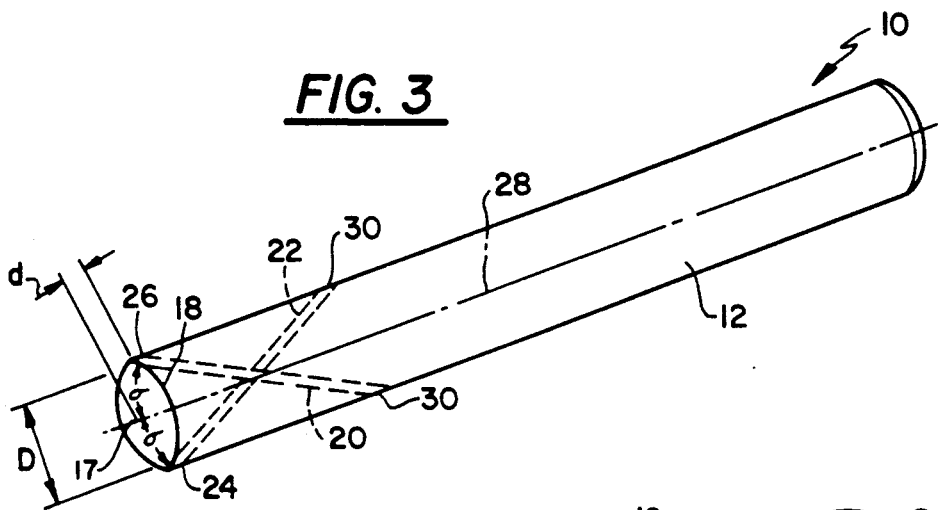
FIG. 3 is a further perspective view of the suture knot making device shown in FIG. 1, but with the suture eliminated.

Referring to the drawings, a suture knot making device is generally indicated at 10. The device 10 is constructed from a solid cylindrical member 12, preferably of plastic. The device has a distal end 14 and a proximal end 16. The diameter of the device 10 is approximately 5.4 mm and its length is preferably about 230 mm. These dimensions enable the device to penetrate deeply into an opening leading to a remote surgical site. As shown in FIGS. 2 and 3, the distal end 14 of the device is of convex shape, the function of which will become apparent below. The convex shape is configured so that the distance (d) (FIG. 3), along member 12 from the point 17 of axial tangency to distal end 14 to the intersection 18 where the distal end merges with the cylindrical surface of member 12, is approximately 1.5 mm.

In the illustrated embodiment, proximal end 16 is also of convex shape. It can be appreciated, however, that other configurations of the proximal end may be used to define a surface which facilitates the holding of device 10.

Bores 20 and 22 extend through member 12. As shown in FIG. 3, the bores 20, 22 extend between respective openings 24 and 26 located on opposite sides of member 12 adjacent intersection 18, at angles $\sigma$ of approximately 30° with respect to a longitudinal axis 28 of member 12, to respective openings 30 (FIG. 3) located on opposite sides of member 12 intermediate its ends. The bores 20, 22 do not intersect within member 12 and preferably are 1.5 to 2.0 mm in diameter. Further, the open ends 24, 26 of the bores 20, 22 preferably are separated by at least 5.0 mm, as shown by distance (D) in FIG. 3. By so locating the bores ends 24, 26, an optimal horizontal spread of a suture loop is created on the distal end 14 for tying a knot, as will become apparent below.

While it is possible for the bores to intersect, it is preferable that they do not, since non-intersecting bores facilitate proper threading of the suture ends. Moreover, with non-intersecting bores, no entanglement of the suture ends is possible when member 12 is moved towards a remote surgical site.

Figure 1:
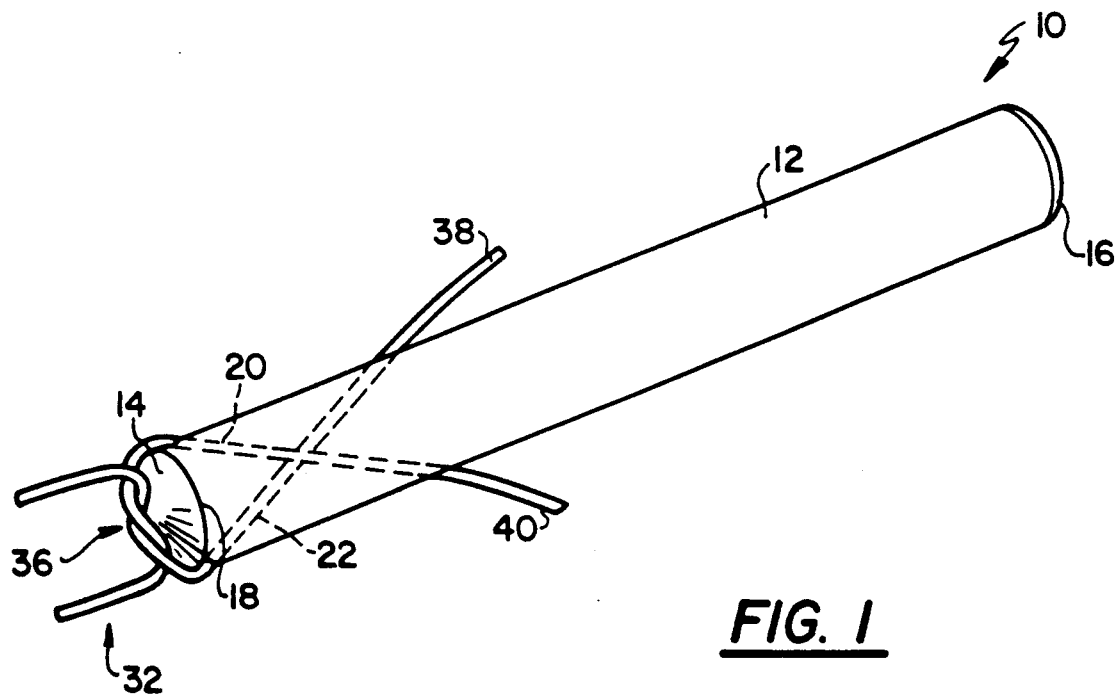
FIG. 1 is a perspective view of a suture knot making device according to the present invention, the device being in operative relationship with a suture.
Figure 4:
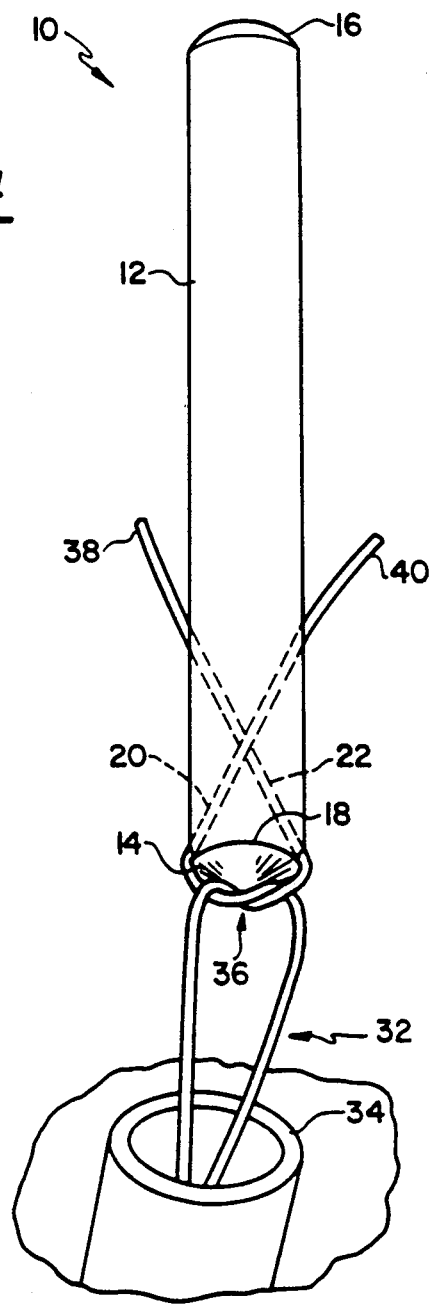
FIG. 4 illustrates a suture loop, disposed on the convex end of the suture knot making device according to FIGS. 1-3, about to be inserted into an opening to a remote surgical site.

A preferred method of using the suture knot making device 10 in an endoscopic procedure will be described with reference to FIGS. 1 and 4. The suture, generally indicated at 32, is looped through, around or into the tissue (not shown) by conventional methods. The ends of the suture are then delivered through a cannula 34 to a location from which the surgeon has access to a remote surgical site. A single loop 36 is made in the suture, and the free ends of the suture are passed through device 10. More particularly, one end 38 of the suture is threaded through bore 22 from the distal end 14 of the device towards the proximal end 16, and the other suture end 40 is threaded in the other bore 20 in a similar fashion. The device 10 next is grasped with one hand at its proximal end 16, while both suture ends 38, 40 are grasped with the other hand. The suture ends are drawn taut so as to position loop 36 against the convex surface of distal end 14. The device 10 is then inserted into the cannula 34 until end 14 is adjacent the surgical site. Further force applied on the suture ends tightens loop 36 onto the suture material which previously had been looped through, around or into the tissue. The suture ends then are released, and the device 10 is gently retracted from the cannula leaving a single knot securing the tissue. If the loop loosens at this juncture, the above procedure is repeated. Additionally, if one or more additional loops are desired, the procedure just described may be repeated.

Inasmuch as the bores 20, 22 cross-over one another within member 12, improved tension and holding of the loop are created when the ends of the suture are pulled from the proximal end of the device. The convexly shaped distal end 14 approximates the same plane which would be created if a surgeon's fingers were tying the knot at the surgical site. The convex surface of the distal end also creates pressure at the center of the loop 36 during its delivery to the surgical site, such pressure deforming the knot upon tying for ensuring the formation of a tight knot.

The method just described is employed when the site for the knot is not readily accessible to the surgeon's fingers. In such a situation, the device 10 is inserted into the opening to the site substantially perpendicular to the ends of the tissue being sutured. There are conditions, however, which permit partial access of the surgeons's fingers so that they can be involved in the formation of a loose knot at the surgical site. The use of the device 10 in such a situation to permit tightening of the knot will be described with reference to FIGS. 5 and 6.

Figure 5:
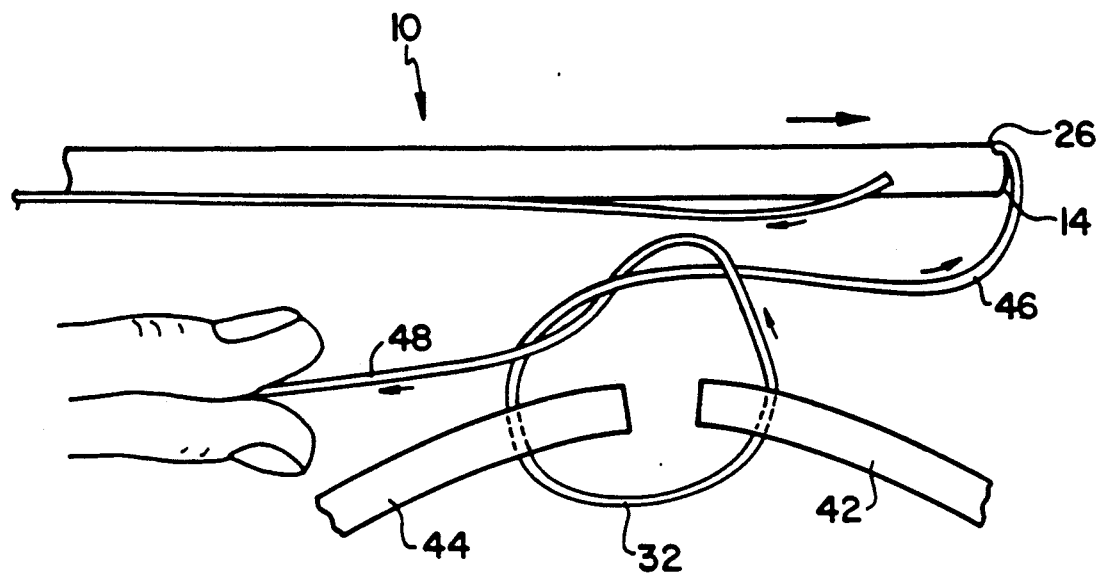
FIGS. 5 and 6 illustrate an alternative method of employing the suture knot making device according to FIGS. 1-3.
Figure 6:
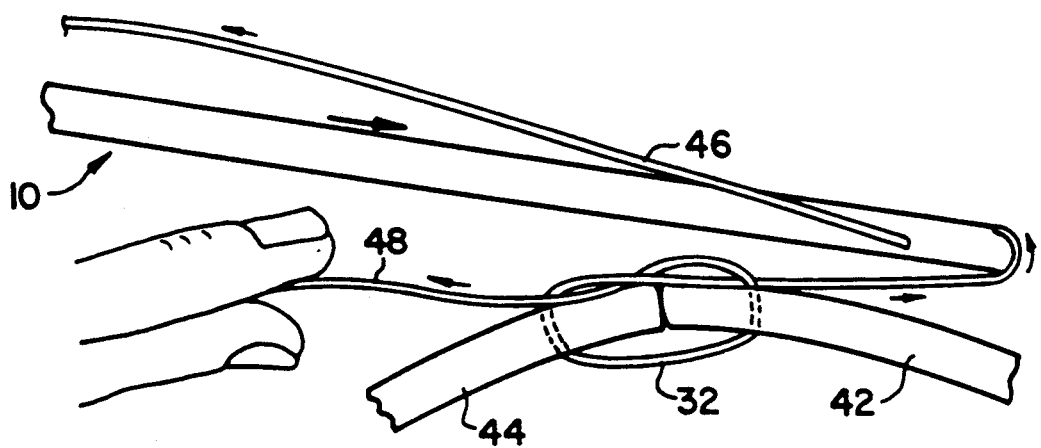

In FIG. 5, ends 42 and 44 of tissue are located at a surgical site to one side of which the surgeon's fingers can approach. A suture 32 is passed through the tissue ends 42 and 44, and a loose loop is formed by the surgeon. End 46 of the suture loop passing through the remote tissue end 44 is inserted in one of the bores (20, 22) of the device 10. End 46 and the opposite end 48 of the loop are grasped by the surgeons's fingers, and the device 10 is moved to the surgical site in a direction substantially parallel with the tissue ends being joined. While being moved, the device 10 is rotated, as required, about its longitudinal axis so that the distal opening 26 of the bore through which suture end 46 passes, is positioned on the opposite side of the device 10 from the knot location. With tension applied to both ends of the suture as the distal end of the device traversed the tissue ends being joined, the device 10 permits the loop to be evenly tightened from both ends due to pressure applied by the device on end 46 of the suture, as shown in FIG. 6. Thus, an acceptably tightened loop is achieved notwithstanding that the suture ends are tensioned in a direction substantially parallel to the plane of the tissue ends being joined.

As stated previously, it is preferable to make the device 10 from plastic rather than other materials, such as metal. Plastic provides a smoother microscopic surface that avoids roughening or breakage of the suture during passage through a cannula and tying. Smoother material allows for more acute angle turns of the suture as it passes through the device, which makes for a tighter knot. Plastic material also permits the bores 20, 22 to be of small diameter to accommodate fine suture threads.

While the invention has been described in connection with what has presently been considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A suture knot making device for positioning a loop of suture at a surgical site remote from an opening to the site, the device comprising:

a cylindrical member having distal and proximal portions, said distal portion having a convexly curved end face, first and second bores disposed in said cylindrical member, each said bore having a distal open end disposed substantially adjacent a transition area where said convexly curved end face merges with a cylindrical surface of said member, said distal open ends being disposed approximately 180° apart, said first and second bores being non-intersecting and extending at an acute angle relative to a longitudinal axis of said member, whereby the bores cross one another within said member.

2. The device as claimed in claim 1, wherein said cylindrical member has a length of approximately 230 mm.

3. The device as claimed in claim 1, wherein a diameter of said cylindrical member is approximately 5.4 mm.

4. The device as claimed in claim 1, wherein a diameter of each said bore is approximately 1.5 to 2.0 mm.

5. The device as claimed in 1, wherein said cylindrical member is formed from plastic material.

6. The device as claimed in claim 1, wherein said acute angle is approximately 30°.

7. The device as claimed in claim 1, wherein each said bore has a proximal open end located intermediate opposite ends of the cylindrical member.

8. A method for forming a suture knot at a remote surgical site, comprising the steps of:
    positioning a length of suture in engagement with tissue at the remote site;
    delivering ends of the suture through an opening to the remote site;
    creating a loop in the delivered ends of the suture;
    threading ends of the suture loop through respective first and second bores formed in a cylindrical member of the type having distal and proximal portions, said distal portion being provided with a convexly curved end face which merges with a cylindrical surface of the member at a transition area where distal ends of said bores are disposed approximately 180° apart, said bores extending through the member at an acute angle relative to a longitudinal axis of said member and crossing one another within the member;
    drawing the suture ends through the bores until said loop is positioned against the convexly curved end face of the member;
    inserting the member into said opening while maintaining the suture ends taut until the convexly curved end face is located adjacent the surgical site;
    applying additional force to the suture ends to tighten the loop against the suture which engages the tissue at the remote surgical site; and
    releasing the suture ends and withdrawing said member from the opening.

9. A method for forming a suture knot in tissue at a remote surgical site, comprising the steps of:
    positioning a length of suture in engagement with tissue at the remote site;
    creating a loop in first and second ends of the suture;
    threading the first end of the suture loop through a bore formed in a cylindrical member of the type having distal and proximal portions, said distal portion being provided with a convexly curved end face which merges with a cylindrical surface of the member at a transition area, said bore extending through the member at an acute angle relative to a longitudinal axis of said member;
    moving the member past the surgical site in a direction substantially parallel to said tissue, said member being oriented during movement so that a portion of said suture is positioned against the convexly curved end face of the member;
    applying tension to the first and second suture ends in a plane substantially parallel to the tissue so as to tighten the loop; and
    releasing the suture ends and removing the member from the remote site.

* * * * *